| United States Patent [19] | [11] | 4,289,785 |
|---|---|---|
| Wilks | [45] | Sep. 15, 1981 |

[54] METHOD AND COMPOSITIONS INVOLVING PROSTAGLANDINS

[75] Inventor: John W. Wilks, Portage, Mich.

[73] Assignee: The Upjohn Company, Kalamazoo, Mich.

[21] Appl. No.: 175,467

[22] Filed: Aug. 6, 1980

[51] Int. Cl.³ ............... A61K 31/335; A61K 31/215; A61K 31/19; A61K 31/165
[52] U.S. Cl. .................... 424/279; 424/305; 424/308; 424/317; 424/324
[58] Field of Search ............ 424/305, 317, 279, 324, 424/308

[56] References Cited

U.S. PATENT DOCUMENTS

| 3,864,387 | 2/1975 | Nelson | 424/317 |
|---|---|---|---|
| 3,978,229 | 8/1976 | Matsumoto | 424/305 |
| 4,045,449 | 8/1977 | Bundy | 424/279 |

*Primary Examiner*—Sam Rosen
*Attorney, Agent, or Firm*—Lawrence T. Welch

[57] ABSTRACT

5-Oxa-17-phenyl-18,19,20-trinor-$PGF_1\alpha$ alkyl esters and 5-oxa-17-phenyl-18,19,20-trinor $PGF_1\alpha$ amide are combined with certain other prostaglandins in synergistic combinations to induce menses in female primates, preferably humans. These synergistic prostaglandin compositions have improved efficacy and safety.

14 Claims, No Drawings

METHOD AND COMPOSITIONS INVOLVING PROSTAGLANDINS

BACKGROUND OF THE INVENTION

This invention relates to a novel synergistic combination of prostaglandin compounds used to induce menses and interrupt early pregnancy in female primates, particularly humans. This invention further provides compositions to be used in this method.

The prostaglandins are derivatives of prostanoic acid which has the structure and carbon atom numbering as shown in formula I. The prostaglandins combined in the present invention are those of the 9-deoxo-9-methylene E series, having the substituents on the cyclopentane ring as shown in formula II, and those of the F$\alpha$ series, having the substituents on the cyclopentane ring as shown in FIG. III. For a fuller discussion of the prostaglandins see e.g., Bergstrom et al. Pharmacol. Rev. 20:1 (1968), and references cited therein. For a fuller discussion of prostaglandin nomenclature see, e.g., N. A. Nelson, Journal of Medicinal Chemistry, 17:911 (1974).

The prostaglandins are useful for a wide variety of pharmacological purposes. Thus compounds of the F$\alpha$ series are useful in stimulating smooth muscle, inhibiting gastric secretion, decongesting nasal passages, decreasing blood platelet adhesion, and for a wide variety of purposes in reproductive medicine, e.g., labor induction, abortion, cervical dilation, regulation of the estrus, and regulation of the menstrual cycle. Compounds of the E series are useful in stimulating smooth muscle, affecting lipolytic activity, inhibiting gastric secretion, controlling spasms and facilitating breathing in asthmatic conditions, decongesting nasal passages, decreasing blood platelet adhesion, and for a wide variety of uses in reproductive medicine, e.g., labor induction, abortion, cervical dilation, regulation of the estrus, and regulation of the menstrual cycle.

The present invention is concerned with the use of prostaglandins for menses induction. More particularly, the present invention relates to menses induction accompanied by pregnancy termination. Thus, the phrases "menses induction", "induction of menses", and the like are meant to include pregnancy termination if the subject is pregnant.

While a number of prostaglandins have been shown to be effective luteolytic agents in various animal tests, it is difficult to find a prostaglandin which is 100% effective in inducing menses in female primates with little or no toxicity or side effects. ("Luteolytic" agents are those which cause corpus luteum regression. A functional corpus luteum is essential in early pregnancy).

It has been demonstrated that combinations of certain prostaglandins of the F series and the E series are effective in inhibiting nidation (implantation of the ovum) in rats and hamsters, as disclosed in U.S. Pat. No. 3,978,229. However, the teachings of the prior art are of limited value in assessing the existence of primate luteolytic activity in that it is not possible to predict accurately the luteolytic activity of a prostaglandin combination in primates using rodent data. See e.g., "The Use of PG's in Human Reproduction", *Population Reports*, Population Information Program, The Johns Hopkins University, Prostaglandins, Series G, No. 8, (March 1980); and J. W. Wilks, "A Procedure for Evaluating Luteolytic Agents in Primates", *Ovarian Follicular And Corpus Luteum Function* C. P. Channing, et al., Eds., pp. 757–766 (Plenum Press, New York 1979).

Various control mechanisms exist governing corpus luteum function in mammalian species. The uterus apparently regulates corpus luteum function in infraprimate animals, but the role of the uterus in primate luteal function has not been established. Thus, while PGF$_2\alpha$, a physiologic luteolytic substance of uterine origin, has been successfully employed to regulate estrous cycles of domestic animals (J. W. Lauderdale, et al., J. Anim. Sci. 38:964 (1974)), it was ineffective in controlling the human corpus luteum (W. J. LeMaire, et al., Prostaglandins 1:259 (1972)).

An effective luteolytic method of inducing menses in females must be able to counteract the corpus luteum stimulating effects of chorionic gonadotropin. Agents which have been shown to be effective during nonfertile menstrual cycles have been ineffective during early gestation and in nonpregnant women given exogenous human chorionic gonadotropin (hCG). See, e.g. J. W. Wilks, supra, and references cited therein.

An additional problem with the prior art combinations is the acute toxicity of some of the prostaglandins employed therein. For example, 16,16-dimethyl PGE$_2$ is part of the most potent luteolytic combination disclosed in U.S. Pat. No. 3,978,229. (The other prostaglandin is 15(S), 16(R)-dimethyl PGF$_2\alpha$). However, the "synergistic" combination employed in the rat included 250 $\mu$g/kg of body weight of 16,16-dimethyl PGE$_2$, which is very toxic in primates, causing convulsions and death at doses as low as 100 $\mu$g/kg of body weight.

It has surprisingly and unexpectedly been found that the prostaglandin combinations of the present invention produce a synergistic menses inducing effect in female primates. These synergistic prostaglandin combinations are virtually 100% effective using low doses of the compounds, essentially without side effects.

PRIOR ART

Combinations of prostaglandins for a variety of purposes have been shown in U.S. Pat. No. 3,978,229. The prostaglandins employed in the method herein have also been disclosed. 5-oxa-17-phenyl-18,19,20-trinor-PGF$_1\alpha$, and its alkyl esters are disclosed in U.S. Pat. No. 3,864,387. 9-deoxo-16,16-dimethyl-9-methylene-PGF$_2$ is disclosed in U.S. Pat. No. 4,165,436. Prostaglandin F$_2\alpha$, 1,15-lactone is disclosed in U.S. Pat. No. 4,045,449. 5-oxa-17-phenyl-18,19,20-trinor-PGF$_1\alpha$ amide is disclosed in U.S. Pat. No. 4,081,478.

SUMMARY OF THE INVENTION

The present invention comprises a method for inducing menses in a female primate which comprises concomitantly administering to said primate an amount effective to induce menses of (1) a prostaglandin of the formula IV, wherein R$_{10}$ is NH$_2$ or —OR$_{20}$ and R$_{20}$ is hydrogen, alkyl of from one to 12 carbon atoms or a pharmacologically acceptable cation, and (2) a prostaglandin of the formula V, wherein R$_{20}$ is defined as above, R$_{20}$ in formulas IV and V being the same or different, or PGF$_2\alpha$ 1,15-lactone.

This invention also provides a pharmaceutical composition comprising (1) a prostaglandin of the formula IV, wherein R$_{10}$ is NH$_2$ or —OR$_{20}$, and R$_{20}$ is hydrogen, alkyl of from one to 12 carbon atoms or a pharmacologically acceptable cation; and (2) a prostaglandin of the formula V, wherein $R_{20}$ is defined as above, $R_{20}$ in formulas IV and V being the same or different, or PGF$_2\alpha$ 1,15-lactone.

Thus, the prostaglandins involved in the combinations of this invention are 5-oxa-17-phenyl-18,19,20-trinor PGF$_1\alpha$, and its alkyl esters; 5-oxa-17-phenyl-18,19,20-trinor-PGF$_1\alpha$ amide; 9-deoxo-16,16-dimethyl-9-methylene-PGE$_2$ and its alkyl esters; and PGF$_2\alpha$ 1,15-lactone.

Examples of alkyl of one to 12 carbon atoms include methyl, ethyl, propyl, butyl, pentyl, hexyl, heptyl, octyl, nonyl, decyl, undecyl, dodecyl, and isomeric forms thereof.

The combinations of the present invention are administered to female primates, including humans, at any point in time during the reproductive cycle starting from ovulation and continuing through the first trimester of pregnancy to inhibit pregnancy and cause menstruation. The method of this invention is advantageously employed in early pregnancy, when menses is delayed, or prior to the occurrence of menses.

The prostaglandin combinations of the present invention are preferably administered up to the eighth week of pregnancy to inhibit corpus luteum function and effectively terminate pregnancy.

Thus the method and combinations of the present invention are effective in inducing menses during early pregnancy, just prior to expected menstruation, or when menstruation is delayed up to 90 days. The method and combinations of this invention are not efficacious in late pregnancy, particularly in the third trimester.

While the method of this invention is effective in all menstruating primates, humans are the most preferred primates for this method.

The effective total dosages of the combined prostaglandins generally fall within the range of 0.1 mg to about 50 mg per kg of body weight, when administered intramuscularly. Equivalent dosages for other routes of administration are alternatively employed. The weight ratios of the prostaglandins in the combinations are dependent upon the prostaglandins employed. The total dosage used depends on the route of administration.

Thus, when 5-oxa-17-phenyl-18,19,20-trinor PGF$_1\alpha$ or an alkyl ester thereof and 9-deoxo-16,16-dimethyl-9-methylene-PGE$_2$ or an alkyl ester thereof are employed in the combination, weight ratios of the PGF$_1\alpha$ compound to PGE$_2$ compound of from 2:1 to 20:1 are preferred. When PGF$_2\alpha$, 1,15-lactone is employed, weight ratios of the PGF$_1\alpha$ compound to lactone compound to from 2:1 to 5:1 are preferred.

Similarly, when the prostaglandin combination employed is 5-oxa-17-phenyl-18,19,20-trinor-PGF$_1\alpha$, amide and 9-deoxo-16,16-dimethyl-9-methylene PGE$_2$, or an alkyl ester thereof, weight ratios of PGF$_1\alpha$, amide compound to PGE$_2$ compound of from 5:1 to 30:1 are preferred.

The weight ratio and total effective dosage used are readily determined by a physician based upon the factors given below.

The "total dosage", as used herein, refers to the total amount of the prostaglandin combination employed to achieve the desired result—i.e., menses induction. This total dosage may be administered all at once, e.g., as a single injection, or over a short time period, e.g., injections every eight hours for several days.

These prostaglandin combinations are administered using sterile pharmaceutical formulations suitable for intavenous infusion, subcutaneous injection, or intramuscular injections. These compounds are also administered by nasal, oral, buccal, intravaginal, intracervical, intrauterine and rectal means. These prostaglandin combinations may be formulated into slow-release vehicles or polymers, such as silicone rubber, to form physical devices for subcutaneous, intravaginal, intracervical, or intrauterine administration.

These prostaglandins may be administered in a pharmaceutical composition containing them, or they may be concomitantly administered to the primate using separate formulations.

The effect of the administration of the combinations of the present invention is superior to the effect of the administration of any one of the prostaglandins alone. The prostaglandin combinations of the present invention show increased efficacy over the use of any of the prostaglandins separately. It is, of course, highly desirable that a menses inducing agent be 100% effective. The dosage required for any one of the prostaglandins disclosed herein to inhibit pregnancy 100% if employed separately is significantly higher than the total combined dosages of the synergistic prostaglandin compounds of this invention.

The greatly decreased dosage of prostaglandins necessary for the method of this invention greatly increases the safety of their use. The method of this invention can be employed with few if any of the common side effects, such as nausea, fever, and diarrhea. Prostaglandins of the E series, for example, are noteably thermogenic at the dosages frequently employed for menses induction. Diarrhea of nausea are also frequent side effects at higher dosages. These higher dosages have also been known to cause death. Therefore the significantly lower dosages employed in the method of this invention represent a surprising and unexpected improvement over the prior art.

As noted above, a problem with finding menses induction agents for primates (e.g., humans) is that agents which have shown good luteolytic activity in rodents such as rats and hamsters frequently are not effective in inducing menses in primates.

Thus, 9-deoxo-16,16-dimethyl-9-methylene-PGE$_2$ by itself is not very effective as an antifertility agent in hamsters, but is very effective in combination with 5-oxa-17-phenyl-18,19,20-trinor-PGF$_1\alpha$, methyl ester for menses induction, as seen by the example below.

While all of the combinations disclosed herein are virtually 100% effective in inhibiting pregnancy in primates at the effective dose, the combination using 5-oxa-17-phenyl-18,19,20-trinor-PGF$_1\alpha$, methyl ester and 9-deoxo-16,16-dimethyl-9-methylene-PGE$_2$ is most preferred.

Pharmacologically acceptable salts of the formulas IV and V compounds useful for the purposes described above are those with pharmacologically acceptable metal cations, ammonium, amine cations, or quaternary ammonium cations.

Especially preferred metal cations are those derived from the alkali metals, e.g., lithium, sodium, and potassium, and from the alkaline earth metals, e.g., magnesium and calcium, although cationic forms of other metals, e.g., aluminum, zinc, and iron are within the scope of this invention.

Pharmacologically acceptable amine cations are those derived from primary, secondary, or tertiary amines. Examples of suitable amines are methylamine, dimthylamine, trimethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, and like aliphatic, cycloaliphatic and araliphatic amines containing up to and including about 18 carbon atoms, as well as heterocyclic amines, e.g., piperidine, morpholine, pyrrolidine, piperazine, and lower-alkyl derivatives thereof, e.g., 1-methylpiperidine, 4-ethylmorpholine, 1-isopropylpyrroldine, 2-methylpyrrolidine, 1,4-dimethylpiperazine, 2-methylpiperidine, and the like, as well as amines containing water-solubilizing or hydrophilic groups, e.g., mono-, di-, and triethanolamine, ethyldiethanolamine, N-butylethanolamine, 2-amino-1-butanol, 2-amino-2-ethyl-1,3-propanediol, 2-amino-2-methyl-1-propanol, tris(hydroxymethyl)aminomethane, N-(p-tert-amylphenyl)diethanolamine, galactamine, N-methylglycamine, N-methylglucosamine, ephedrine, phenylephrine, epinephrine, procaine, and the like.

Examples of suitable pharmacologically acceptable quaternary ammonium cations are tetramethylammonium, tetraethylammonium, benzyltrimethylammonium, phenyltriethylammonium, and the like.

DESCRIPTION OF THE PREFERRED EMBODIMENTS

The method of this invention is seen more fully by the examples given below.

EXAMPLE 1

Induction of menses using 5-oxa-17-phenyl-18,19,20-trinor-PGF$_1$α, methyl ester and 9-deoxo-16,16-dimethyl-9-methylene-PGE$_2$ Part A Six female rhesus monkeys were placed with males from days 11 through 15 of the menstrual cycle. 5 ml blood samples were collected daily between 7 and 9:00 a.m. beginning on day 20 of the menstrual cycle and continued until day 36 from the previous menses. Concentrations of monkey chorionic gonadotropin (mCG), and progesterone were determined for each blood sample by radioimmunoassay.

Pregnancy was confirmed in all monkeys prior to treatment by the qualitative determination of mCG in the serum. Treatments were given by intramuscular injection at 7:00 a.m., 3:00 p.m. and 11:00 p.m. of day 28 from the previous menses. Prostaglandins were given as an emulsion in 1 ml of 4% glass distilled ethanol 96% sterile aqueous vehicle, containing 10 mg of caboxymethylcellulose, 4 mg of polysorbate 80, and 0.42 mg of propylparaben per milliter. The dose of 5-oxa-17-phenyl-18,19,20-trinor-PGF$_1$α, methyl ester at each injection was 7.5 mg for a total dose of 22.5 mg. The dose of 9-deoxo-16,16-dimethyl-9-methylene-PGE$_2$ at each injection was 0.5 mg for a total dose of 1.5 mg. For the three monkeys in which the compounds were given in combination, the prostaglandins were mixed together in the same vehicle and given at the same injection site.

Three of the monkeys were given the combination of prostaglandins, while three of the monkeys were given 9-deoxo-16,16-dimethyl-9-methylene-PGE$_2$ alone.

Pregnancy terminated promptly in the three monkeys given the combination of prostaglandins. Pregnancy terminated in one of the three monkeys given the PGE$_2$ analog alone, and this failure of gestation was delayed for four weeks after prostaglandin treatment. Vaginal bleeding commenced on the day after treatment in two of the monkeys treated with the combination of prostaglandins, and vaginal bleeding began on the second day following prostaglandin administration in the third monkey treated with the prostaglandin combination.

Serum progesterone and mCG declined to 10% of pretreatment values within 24 hours of initial treatment. Progesterone remained depressed throughout the study, and mCG disappeared from the blood.

Slight anorexia was observed in one of the combination-treated monkeys on day of treatment, while no side effects were observed in the other two monkeys.

Part B

Following the procedure of Part A, three pregnant rhesus monkeys were given a single injection of 7.5 mg of 5-oxa-17-phenyl-18,19,20-trinor-PGF$_1$α, methyl ester and 0.5 mg of 9-deoxo-16,16-dimethyl-9-methylene-PGE$_2$ at 7:00 A.M. on day 28 of the menstrual cycle. Progesterone and mCG dropped to 10% of pretreatment levels within 24 hours of injection. Pregnancy terminated promptly in all three monkeys; menstrual bleeding was first observed on the day of treatment, the day after treatment, and 8 days after treatment, respectively, for the three monkeys. No side effects were observed in any of the monkeys.

EXAMPLE 2

Induction of menses using 5-oxa-17-phenyl-18,19,20-trinor-PGF$_1$α, methyl ester and PGF$_2$α, 1,15-lactone Using the procedure of the preceeding example, three rhesus monkeys were given three 5 mg injections of 5-oxa-17-phenyl-18,19,20-trinor-PGF$_1$α, methyl ester and three 1 mg doses of PGF$_2$α 1,15-lactone. The prostaglandins were mixed together in the same vehicle and given at the same injection site.

Pregnancy was terminated in all three monkeys. Pregnancy was promptly terminated in two monkeys. For these monkeys, progesterone and mCG declined markedly within 24 hours of treatment and remained depressed throughout the study. Serum progesterone and mCG declined in the third monkey and remained depressed throughout the study. This monkey was no longer pregnant 18 days after blood sampling was completed.

Slight appetite depression was observed on the day of treatment of all three monkeys. The animals ate approximately two thirds of the food provided them, however, no other side effects were seen.

EXAMPLE 3

Induction of menses using 5-oxa-17-phenyl-18,19,20-trinor-PGF$_1$α, methyl ester alone Part A Following the procedure of Example 1, 7.5 mg of 5-oxa-17-phenyl-18,19,20-trinor-PGF$_1$α, methyl ester in one ml of sterile vehicle, were injected on days 28 and 29 of the menstrual cycle to each of two monkeys, and on days 27 and 28 for one monkey, at 7:00 A.M. and 7:00 P.M. Another 3 monkeys were injected with sterile vehicle only, following the same regimen, on days 28 and 29.

Pregnancy was terminated in one of the monkeys receiving the prostaglandin compound. Serum progesterone declined below 1 ng/ml within 24 hours of initial treatment and remained depressed throughout the study. Serum progesterone declined to 75% of normal in the other two treated monkeys within 24 hours of initial treatment, but rebounded to normal despite continued treatment.

Slight diarrhea was observed in two of the treated monkeys, and all three did not eat all their food on days of treatment.

Part B

Following the procedure of Example 1, Part A, nine 7.5 mg injections of 5-oxa-17-phenyl-8,19,20-trinor-PGF$_1\alpha$, methyl ester were administered to each of two pregnant monkeys. The total dosage was 67.5 mg per monkey. Pregnancy terminated in one monkey. The monkeys experienced slight appetite depression on the days of treatment.

EXAMPLE 4

Induction of menses using PGF$_2\alpha$, 1,15-lactone alone

Using the procedure of Example 3, Part A, two injections of PGF$_2\alpha$, 1,15-lactone were given on day 28 of the menstrual cycle in 3 mg portions to each of three female monkeys.

Pregnancy was terminated in one of the three animals.

EXAMPLE 5

Administration of 5-oxa-17-phenyl-18,19,20-trinor-PGF$_1\alpha$, methyl ester and 9-deoxo-16,16-dimethyl-9-methylene-PGE$_2$ prior to the occurrence of menses Nine female rhesus monkeys of proven fertility were caged with male rhesus monkeys of proven fertility from days 11 through 15 of the menstrual cycle. Female monkeys received intramuscular injections of 1.5 mg of 5-oxa-17-phenyl-18,19,20-trinor-PGF$_1\alpha$ methyl ester and 0.1 mg of 9-deoxo-16,16-dimethyl-9-methylene-PGE$_2$ once daily on days 18 through 22 of the menstrual cycle. The prostaglandins were mixed together in the same vehicle and given at the same injection site. None of the monkeys treated with the combination became pregnant.

EXAMPLE 6

Induction of menses using 5-oxa-17-phenyl-18,19,20-trinor-PGF$_1\alpha$ amide and 9-deoxy-9-methylene-16,16-dimethyl PGE$_2$ Following the procedure of Example 1, three injections, each containing 7.5 mg of the PGF$_1\alpha$ amide and 0.5 mg of the PGE$_2$ compound, were administered to two pregnant rhesus monkeys, in eight hour intervals on day 28 of the menstrual cycle. Pregnancy terminated in both monkeys.

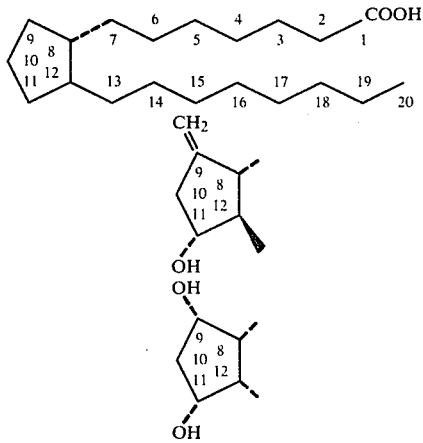

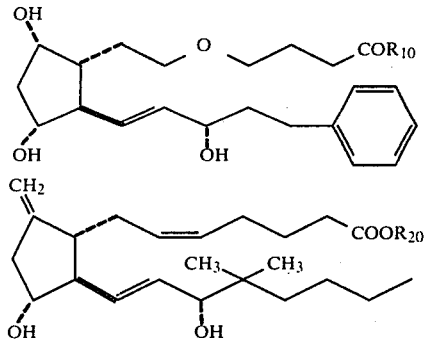

I claim:

1. A method for inducing menses in a female primate which comprises concomitantly administering to said primate an amount effective to induce menses of
   (1) a prostaglandin of the formula IV,

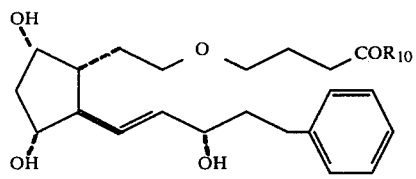

wherein R$_{10}$ is NH$_2$ or —OR$_{20}$ and R$_{20}$ is hydrogen, alkyl of from one to 12 carbon atoms, or a pharmacologically acceptable cation; and either
   (2) a prostaglandin of the formula V,

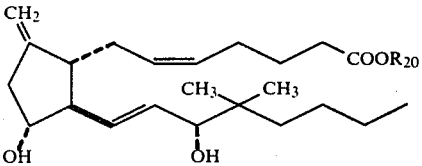

wherein R$_{20}$ is defined as above, R$_{20}$ in formulas IV and V being the same or different, or PGF$_2\alpha$ 1,15-lactone.

2. A method of claim 1 wherein the prostaglandin of Formula IV is 5-oxa-17-phenyl-18,19,20-trinor PGF$_1\alpha$, methyl ester.

3. A method of claim 2 wherein the other prostaglandin is 9-deoxo-16,16-dimethyl-9-methylene-PGE$_2$.

4. A method of claim 2 wherein the other prostaglandin is PGF$_2\alpha$ 1,15-lactone.

5. A method of claim 1 wherein the prostaglandin of Formula IV is 5-oxa-17-phenyl-18,19,20-trinor-PGF$_1\alpha$ amide.

6. A method of claim 5 wherein the other prostaglandin is 9-deoxo-16,16-dimethyl-9-methylene-PGE$_2$.

7. A method of claim 5 wherein the other prostaglandin is PGF$_2\alpha$ 1,15-lactone.

8. A pharmaceutical composition useful for inducing menses in a female primate comprising an amount effective to induce menses of a prostaglandin of the formula IV,

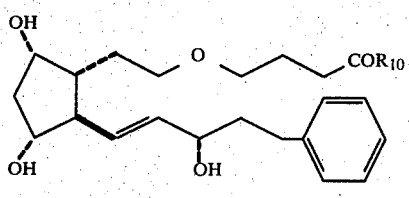

wherein $R_{10}$ is $NH_2$ or $-OR_{20}$ and $R_{20}$ is hydrogen, alkyl of from one to 12 carbon atoms, or a pharmacologically acceptable cation and either (2) a prostaglandin of the formula V,

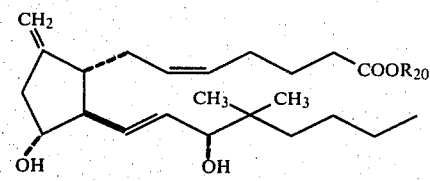

wherein $R_{20}$ is defined as above, $R_{20}$ in formulas IV and V being the same or different, or $PGF_2\alpha$ 1,15-lactone.

9. A composition of claim 2 wherein the prostaglandin of Formula IV is 5-oxa-17-phenyl-18,19,20-trinor $PGF_1\alpha$, methyl ester.

10. A composition of claim 9 wherein the other prostaglandin is 9-deoxo-16,16-dimethyl-9-methylene-$PGE_2$.

11. A composition of claim 9 wherein the other prostaglandin is $PGF_2\alpha$ 1,15-lactone.

12. A composition of claim 2 wherein the prostaglandin of Formula IV is 5-oxa-17-phenyl-18,19,20-trinor $PGF_1\alpha$ amide.

13. A composition of claim 12 wherein the other prostaglandin is 9-deoxo-16,16-dimethyl-9-methylene-$PGE_2$.

14. A composition of claim 12 wherein the other prostaglandin is $PGF_2\alpha$ 1,15-lactone.

* * * * *

UNITED STATES PATENT OFFICE
CERTIFICATE OF CORRECTION

Patent No. 4,289,785         Dated September 15, 1981

Inventor(s)   John W. Wilks

It is certified that error appears in the above-identified patent and that said Letters Patent are hereby corrected as shown below:

olumn 4, line 32, "Diarrhea of" should read -- Diarrhea and --.
olumn 4, line 68, "dimthylamine," should read -- dimethylamine, --.
olumn 5, line 50, "caboxymethylcellulose," should read -- carboxymethyl-
   cellulose, --.
olumn 7, line 51, "   " should read -- FORMULAS --.
olumn 7, line 66, that portion of the formula should read as follows:

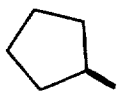   III

Signed and Sealed this

Third Day of August 1982

[SEAL]

Attest:

GERALD J. MOSSINGHOFF

*Attesting Officer*   *Commissioner of Patents and Trademarks*